United States Patent [19]

Strauss

[11] Patent Number: 4,934,832

[45] Date of Patent: Jun. 19, 1990

[54] COMPUTER TOMOGRAPHY APPARATUS WITH RESILIENTLY MOUNTED RADIATION DETECTOR

[75] Inventor: Karl-Ernst Strauss, Spardorf, Fed. Rep. of Germany

[73] Assignee: Siemens Aktiengesellschaft, Berlin and Munich, Fed. Rep. of Germany

[21] Appl. No.: 354,207

[22] Filed: May 19, 1989

[30] Foreign Application Priority Data

May 25, 1988 [DE] Fed. Rep. of Germany ....... 3817724

[51] Int. Cl.$^5$ ............................................. G03B 41/16
[52] U.S. Cl. ....................................... 378/14; 378/11; 378/4; 378/19
[58] Field of Search ................... 378/4, 14, 7, 12, 137, 378/138, 162, 16, 15, 19, 11

[56] References Cited

U.S. PATENT DOCUMENTS

| | | | |
|---|---|---|---|
| 3,934,142 | 1/1976 | Hounfield | 378/11 |
| 4,002,917 | 1/1977 | Mayo . | |
| 4,211,925 | 7/1980 | Fairbairn . | |
| 4,417,354 | 11/1983 | Pfeiler | 378/4 |
| 4,837,792 | 6/1989 | Goethert | 378/4 |
| 4,850,004 | 7/1989 | Saito et al. | 378/4 |

FOREIGN PATENT DOCUMENTS

53-132985 11/1978 Japan .
1492596 1/1975 United Kingdom .

*Primary Examiner*—Janice A. Howell
*Assistant Examiner*—Don Wong
*Attorney, Agent, or Firm*—Hill, Van Santen, Steadman et al.

[57] ABSTRACT

A computer tomograph apparatus of the type having a rotating frame which carriers an x-ray source and a radiation detector includes a mount for the radiation detector which resiliently seats the radiation detector on the rotating frame permitting slight displacement of the radiation detector in a direction tangent to the orbit of the detector around a patient. The resilient mounting of the radiation detector suppresses the transmission of mechanical jolts and other jarring forces from the rotating frame to the detector. Because of the resilient mounting, the weight of the radiation detector will cause a slight dislocation of the detector during a revolution. To compensate for this dislocation the rated position of the focus is determined dependent upon the detector position, so that the position of the focus can be adjusted corresponding to this detector displacement.

2 Claims, 1 Drawing Sheet

COMPUTER TOMOGRAPHY APPARATUS WITH RESILIENTLY MOUNTED RADIATION DETECTOR

BACKGROUND OF THE INVENTION

1. Field of the Invention

The present invention is directed to a computer tomography apparatus of the type wherein an x-ray source and a radiation detector are rotated on a frame around a patient, and in particular to such a computer tomography apparatus wherein the detector is resiliently mounted on the frame permitting slight displacement of the detector in a direction tangent to the orbit of the detector around the patient.

2. Description of the Prior Art

Computer tomography devices are known in the art wherein an x-ray source and a radiation detector are mounted on a frame which is rotated around a patient. The radiation detector consists of a row of detector elements, and the x-ray source emits a fan-shaped x-ray beam in which the patient is disposed. The frame, with the x-ray source and the radiation detector carried thereon, is rotated around the patient so that the patient is irradiated by the x-ray beam from different directions. The axis of rotation of the frame is perpendicular to the plane containing the x-ray beam. Radiation attenuated by the patient is incident on the x-ray detector, which converts the radiation into electrical signals. The signals are supplied to a computer which constructs a cross-sectional image (slice) of the examination subject from the measured values of the radiation detector.

It is also known to provide such a computer tomography apparatus with means for deflecting the focus of the x-ray source in the fan plane perpendicular to an axis of symmetry of the radiation detector. This results in an increased total number of image values, and thus achieves an improved image resolution in comparison with operation wherein the focus has a fixed position. The rated or known position of the focus is prescribed relative to the rotating frame, because in conventional devices the radiation detector is stationarily mounted on the rotating frame, and is therefore assumed to have fixed and unchanging position relative to the frame. Because of this rigid mounting, however, mechanical forces are transmitted from the frame to the radiation detector, and jolts and other jarring forces acting on the frame will similarly jolt or jar the radiation detector, possibly giving rise to noise signals leading to image artifacts.

SUMMARY OF THE INVENTION

It is an object of the present invention to provide a computer tomography apparatus of the type described above wherein jarring of the rotating frame has substantially no influence on the quality of the image.

The above object is achieved in accordance with the principles of the present invention in a computer tomography apparatus wherein the radiation detector is resiliently mounted on the rotating frame tangentially relative to its orbit. Control means are provided for determining the rated position of the focus of the x-ray source dependent upon the respective detector position. Because of the resilient mounting of the radiation detector, jarring of the rotating frame has substantially no influence on the image quality, because the jarring forces are not transmitted to the detector through the mount. In other words, the mount substantially insulates the radiation detector from such jarring forces which act on the frame. Because of the resilient mounting, however, the radiation detector will be displaced slightly during a revolution of the frame due to the force of gravity. This movement will be in a direction tangential to the orbit of the radiation detector, and the displacement will be of a calculable value. The rated position of the focus in the x-ray source is correspondingly displaced by the same unit which is used to displace the focus to obtain improved image quality. The slight displacement of the radiation detector thus does not result in a change in the measured values, and thus does not cause image errors.

DESCRIPTION OF THE PREFERRED EMBODIMENTS

Figure 1:
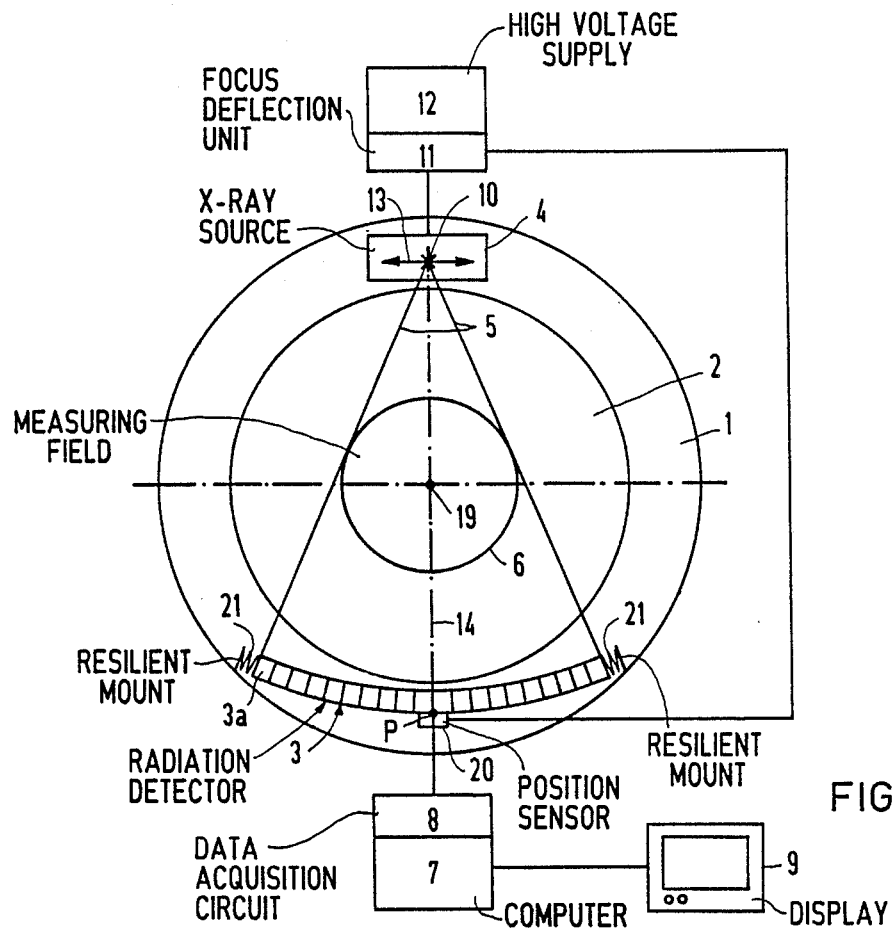
FIG. 1 is a schematic block diagram of a computer tomography apparatus constructed in accordance with the principles of the present invention.

As shown in FIG. 1, a computer tomography apparatus constructed in accordance with the principles of the present invention has a rotating frame 1 which surrounds a measuring opening 2. A radiation detector 3, consisting of a row of detector elements such as element 3a, and an x-ray source 4 are mounted on the frame 1. The x-ray source 4 generates a fan-shaped x-ray beam 5 which transirradiates a measuring field 6. An examination subject, for example a patient on a bed, is disposed in the measuring field 6. As the frame 1 is rotated around an axis 19, which extends through the measuring opening 2 and the measuring field 6 perpendicular to the plane containing the fan-shaped beam 5, the examination subject is irradiated from different directions. The radiation attenuated by the patient is incident on the radiation detector 3, and the corresponding measured values are supplied via a data acquisition circuit 8 to a computer 7, which constructs a cross-sectional image (slice) of the examination subject. The image is reproduced on a display 9.

The x-ray source 4 has a focus 10. The focus 10 is periodically deflected in the direction of the double arrow 13, i.e., perpendicular to an axis of symmetry 14 of the radiation detector 3, by a deflection unit 11, which is a part of the high voltage supply 12 for the x-ray source 4. This periodic deflection increases the number of measured values generated by the detector 3, thereby increasing the resolution of the image.

Figure 2:
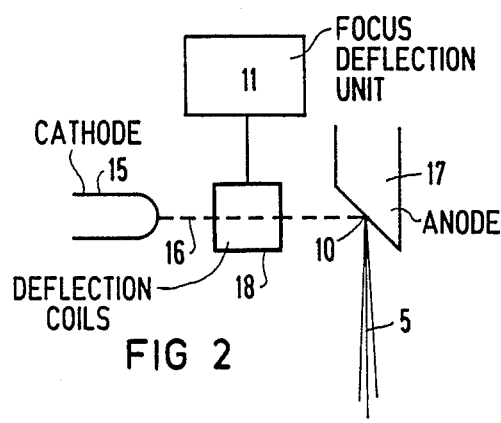
FIG. 2 is a schematic diagram showing a portion of the computer tomography apparatus of FIG. 1 in detail.

Details of this focus deflection are shown in FIG. 2. A cathode 15 emits an electron beam 16 which is incident on an anode 17, from which the x-ray beam 5 emanates, such that the fan plane is perpendicular to the plane of the drawing. The periodic focus deflection perpendicular to the plane of the drawing is undertaken with deflector coils 18 which are connected to the deflection unit 11.

As shown in FIG. 1, the radiation detector 3 is elastically or resiliently mounted by resilient mounts 21. The resilient mounts 21 absorb jolts and other jarring forces acting on the frame 1, so that those forces are not transmitted to the radiation detector 3. The resilient mounts 21 may be of any suitable type, such as springs, pneumatic units, hydraulic units, or the like. The necessary function for the resilient mount 21 is that it be a means for substantially insulating the radiation detector 3 from mechanical jolts and jarring acting on the frame 1.

In the position of the radiation detector 3 shown in FIG. 1, its focus coincides with the focus 10 of the x-ray source. As the frame 1 is rotated, however, due to the resilient mounting of the detector 3, the detector 3 will be dislocated slightly due to its weight. To compensate for this gravity-caused dislocation, the radiation detector 3 is provided with a position sensor 20. The position sensor 20 generates a signal corresponding to the position of the radiation detector 3 as it is rotated by the frame 1. This signal is supplied to the deflection unit 11, so that the focus of the x-ray source is correspondingly deflected to compensate for the slight change in position of the radiation detector 3 relative to the frame 1. The electrical signal which is generated by the sensor 20 corresponds to the locus of a vector of a detector point P.

Given this known movement of the radiation detector 3, the rated position of the focus 10 of the x-ray source, relative to the focusing point of the radiation detector 3, is prescribed. If rF1 is the locus vector of the rated position of the focus 10 for a radiation detector 3 which is stationary relative to the rotating frame 1, and rDU is the locus vector of a detector point P if the radiation detector 3 were fixed relative to the rotating frame 1, rDb is the locus vector of the same detector point P when the radiation detector 3 is resiliently mounted, then the locus vector rF2 for the rated position of the focus 10, which refers to the focusing point of the radiation detector 3, is obtained by the following relationship:

$$rF2 = rF1 + \text{tangential component of the vector } (rDU - rDb).$$

In the exemplary embodiment described above, the dislocation of the rated position of the focus 10 which compensates for the tangential motion of the radiation detector 3 is superimposed with the periodic focus motion for increasing the number of measured values. It is possible, however, to omit this periodic focus deflection.

It is also possible to omit the sensor 20 if the respective locus vector of the detector point P is acquired with reference to a stationary point on the rotating frame 1 in the respective projection. A curve which reproduces the dependency of the locus vector of the detector point P on the respective projection can be stored for this purpose.

The position of the radiation detector 3, for example, can be defined according to the following calculation:

$$t(rDU - rDb) = t_o \cdot \cos \alpha,$$

wherein $t(rDU - rDb)$ is the tangential component of the vector $(rDU - rDb)$, $\alpha$ is the angle made by a straight line proceeding through the focus 10, and disposed perpendicularly on the axis 19, makes with the horizontal in the fan plane, and $t_o$ is a constant characteristic of the combination of the resilient mounts 21 and the detector 3, and corresponds to the amplitude of the tangential excursion of the detector 3.

Although modifications and changes may be suggested by those skilled in the art it is the intention of the inventor to embody within the patent warranted hereon all changes and modifications as reasonably and properly come within the scope of his contribution to the art.

We claim as our invention:

1. A computer tomography apparatus comprising:
   a rotatable frame having a central opening in which an examination subject is disposed, said frame moving in an orbit around said examination subject;
   an x-ray source mounted on said frame having a focus from which a fan-shaped x-ray beam emanates which transirradiates said examination subject;
   a detector attached to said frame and disposed for receiving radiation from said x-ray source attenuated by said patient and generating electrical signals corresponding to the measured radiation, said detector having a detector focus on an axis of symmetry of said detector;
   means for constructing an image of a cross-section of said patient from said signals;
   means for deflecting the focus of said x-ray source in a plane perpendicular to said axis of symmetry of said radiation detector;
   means for resiliently mounting said radiation detector on said frame for permitting slight movement of said radiation detector substantially tangentially relative to the orbit of said radiation detector around said examination subject; and
   means for controlling said means for deflecting said focus to change the position of the focus dependent upon the detector position relative to said frame so that the focus of the x-ray source and the focus of the detector are maintained coincident during rotation of said frame.

2. A computer tomography apparatus as claimed in claim 1, wherein said means for controlling said means for focussing is a means for calculating a locus vector rF2 for the rated position of the focus relative to the focus of the radiation detector according to the following equation:

$$rF2 = rF1 + \text{tangential component of the vector } (rDU - rDb),$$

wherein rF1 is the locus vector of the rated position of the focus, given a stationary radiation detector, with respect to said frame, wherein rDU is the locus vector of a detector point on said radiation detector for a radiation detector which is stationary with respect to said frame, and wherein rDb is the locus of said detector point for the radiation detector resiliently mounted by said means for resiliently mounting.

* * * * *